US00PP16429P3

(12) United States Plant Patent
Chahbandar

(10) Patent No.: US PP16,429 P3
(45) Date of Patent: Apr. 11, 2006

(54) ARTICHOKE PLANT NAMED 'BCV 8-11'

(50) Latin Name: *Cynara scolymus* L.
Varietal Denomination: BCV 8-11

(76) Inventor: Medhat Chahbandar, Domaine La Quintane, Torrielles (FR), 66440

( * ) Notice: Subject to any disclaimer, the term of this patent is extended or adjusted under 35 U.S.C. 154(b) by 0 days.

(21) Appl. No.: 10/371,510

(22) Filed: Feb. 20, 2003

(65) Prior Publication Data

US 2004/0168238 P1 Aug. 26, 2004

(51) Int. Cl.
*A01H 5/00* (2006.01)

(52) U.S. Cl. ..... Plt./258
(58) Field of Classification Search ..... Plt./258
See application file for complete search history.

(56) References Cited

U.S. PATENT DOCUMENTS

PP12,206 P2 11/2001 Cofer
PP12,208 P2 11/2001 Colfer
PP14,578 P2 * 3/2004 Colfer ..... Plt./258

* cited by examiner

*Primary Examiner*—Kent Bell
*Assistant Examiner*—W. C. Haas
(74) *Attorney, Agent, or Firm*—Townsend and Townsend and Crew LLP

(57) ABSTRACT

A new and distinct cultivar of Artichoke plant named 'BCV 8-11', having bracts exhibiting a much darker and vibrant violet hue and reduced pubescence in comparison to the parent variety 'Violet de Provence'. 'BCV 8-11' is sterile and produces more tender fruit and has a greater production of fruit buds than 'Violet de Provence'.

4 Drawing Sheets

Botanical designation: *Cynara scolymus* L.
Variety denomination: 'BCV 8-11'.

BACKGROUND OF THE INVENTION

The present invention comprises a new and distinct cultivar of artichoke plant, botanically known as *Cynara scolymus* L., herein referred to by the cultivar name 'BCV 8-11'. This variety is characterized by bracts having a much darker and vibrant violet or purple hue than the parent 'Violet de Provence' and reduced pubescence with a more tender fruit than the parent. It is sterile, and has a greatly enhanced prolificty, i.e., a greater production of fruit buds per plant in comparison to the parent and other varieties known to the inventor.

*Cynara scolymus* L., commonly known as Globe artichoke, is a perennial herb and is a member of the family Asteraceae, also known as the Compositae family. Globe artichokes comprise: leaves, which are pinnately lobed, but primarily spineless; globose capitula composed of overlapping layers of large involucral bracts; and receptacles, which are enlarged and fleshy. Globe artichoke plants are essentially grown for the production of the immature flower heads (or buds). The immature buds are harvested before the appearance of sexual organs (or the mature flower) and are considered vegetable delicacies. Fresh artichokes may be steamed, boiled, or baked after which the fleshy receptacle, inner and outer bracts, and parts of the floral stem may be eaten.

The new cultivar is a product of a planned breeding program carried out by the inventor near Perpignan, France. It first originated as a single plant, which was obtained from a cross between two 'Violet de Provence' (unpatented) artichokes from the same population. After it was selected as a single plant, it was asexually reproduced under tissue culture stress conditions that caused somaclonal variability and then selected again in the field for red color. A single plant was selected. Further asexual tissue culture propagation revealed that the new cultivar was stable. Specifically, a single plant was selected having a combination of characteristics that were desirable. A classical method of in vitro micropropagation using meristem tips was used to propagate multiple generations. It was demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'BCV 8-11'. These traits in combination distinguish the Artichoke as a new and distinct cultivar. The parent variety listed above is, to the inventor's knowledge, the closes prior art to the claimed plant variety. The bracts of 'BCV 8-11' have much darker and vibrant violet or purple hue than the parent or any other variety known to the inventor. In comparison to the parent variety, it has reduced pubescence, is sterile, produces a more tender fruit, and has been shown to exhibit a greatly enhanced prolificity, ie., a greater production of fruit buds per plant.

'BCV 8-11' has not been observed under all possible environmental conditions. The phenotype of the new cultivar may vary with variations in environment such as temperature, humidity, light intensity and day length, without any change in the genotype. The following observations, measurements and values describe the new cultivar as grown in Lompoc, Calif. under conditions that closely approximate those generally used in horticultural practice.

Lompoc is located on California's central coast in Santa Barbara County. Conditions can vary in the summer months. Air temperatures can range between the low 60's to 80's. The relative humidity is generally high. Prevailing winds are northwesterly and rainfall averages 12 inches per year.

In the following description, holding quality was measured by the physical appearance of the head. This includes the head's appearance following 3- and 7-daystorage periods in cold storage at 34° F. The head's exterior (oxidation) was observed at each of the two observation points. Browning and blackening of plant tissue was evaluated as light, moderate and extreme. Overall storage response was measured by observing heads following 3- and 7-day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, necrotic or chlorotic lesions or any abiotic responses to environmental conditions.

BRIEF DESCRIPTION OF THE DRAWINGS

This new variety is illustrated by the accompanying photographic drawings. The colors in the photographs are as true to those of the plant as can be reasonably obtained from conventional photographic procedures.

DETAILED DESCRIPTION OF THE INVENTION

Figure 1:
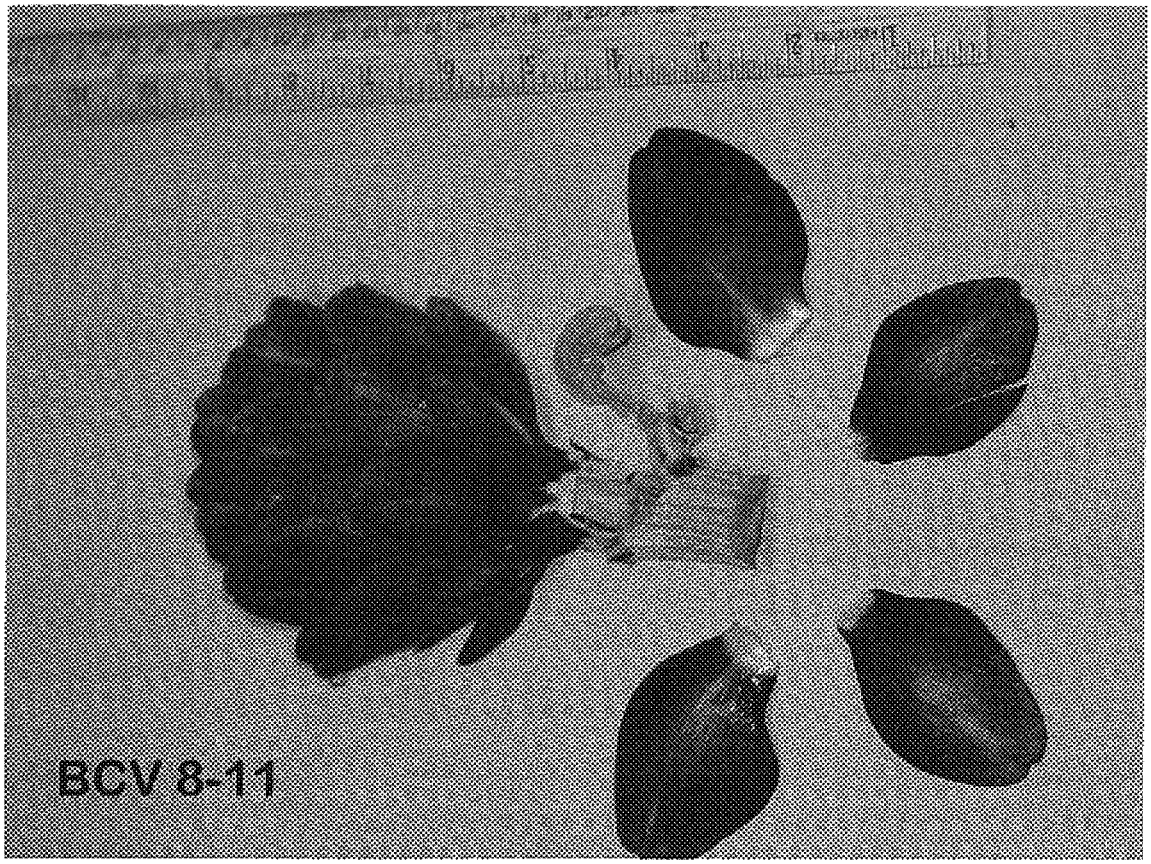
FIG. 1 shows a side elevational view of 'BCV 8-11's fruit in full color.
Figure 2:
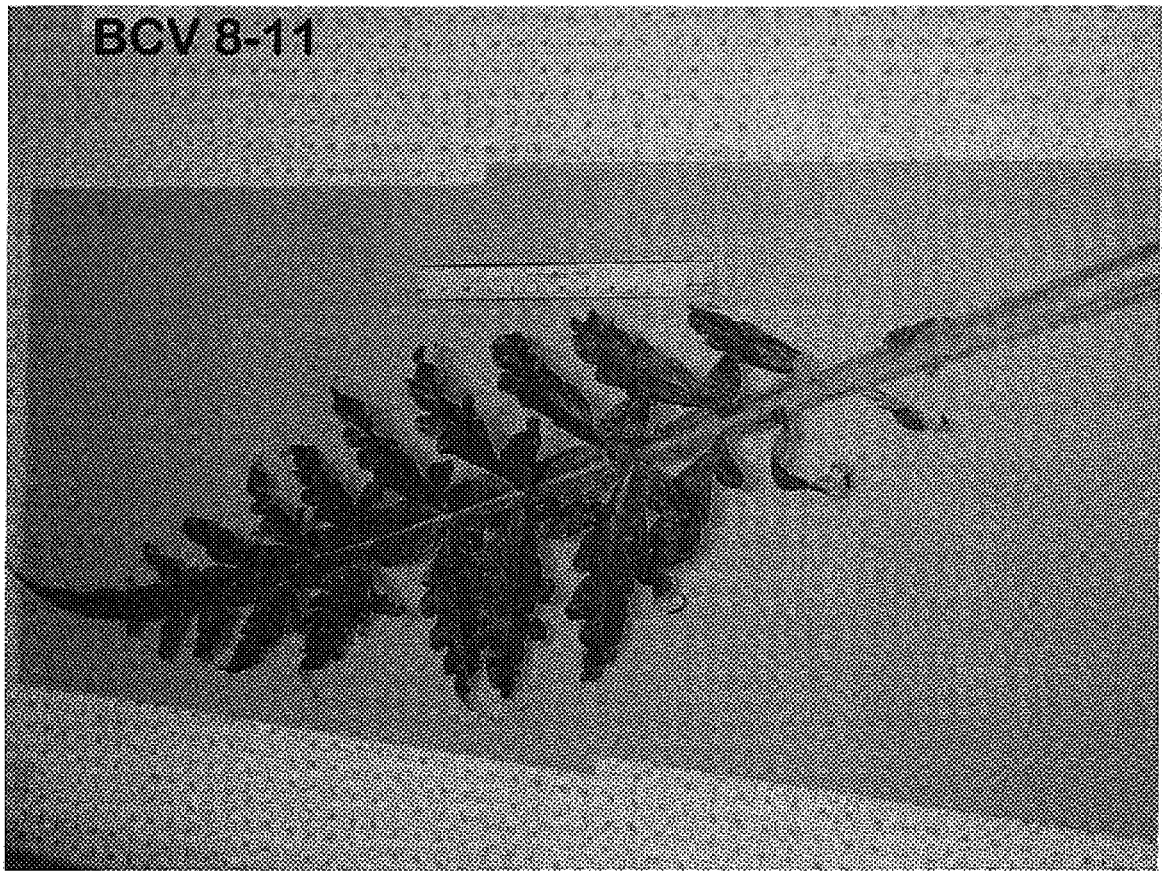
FIG. 2 shows a side elevational view of 'BCV 8-11's foliage in full color.
Figure 3:
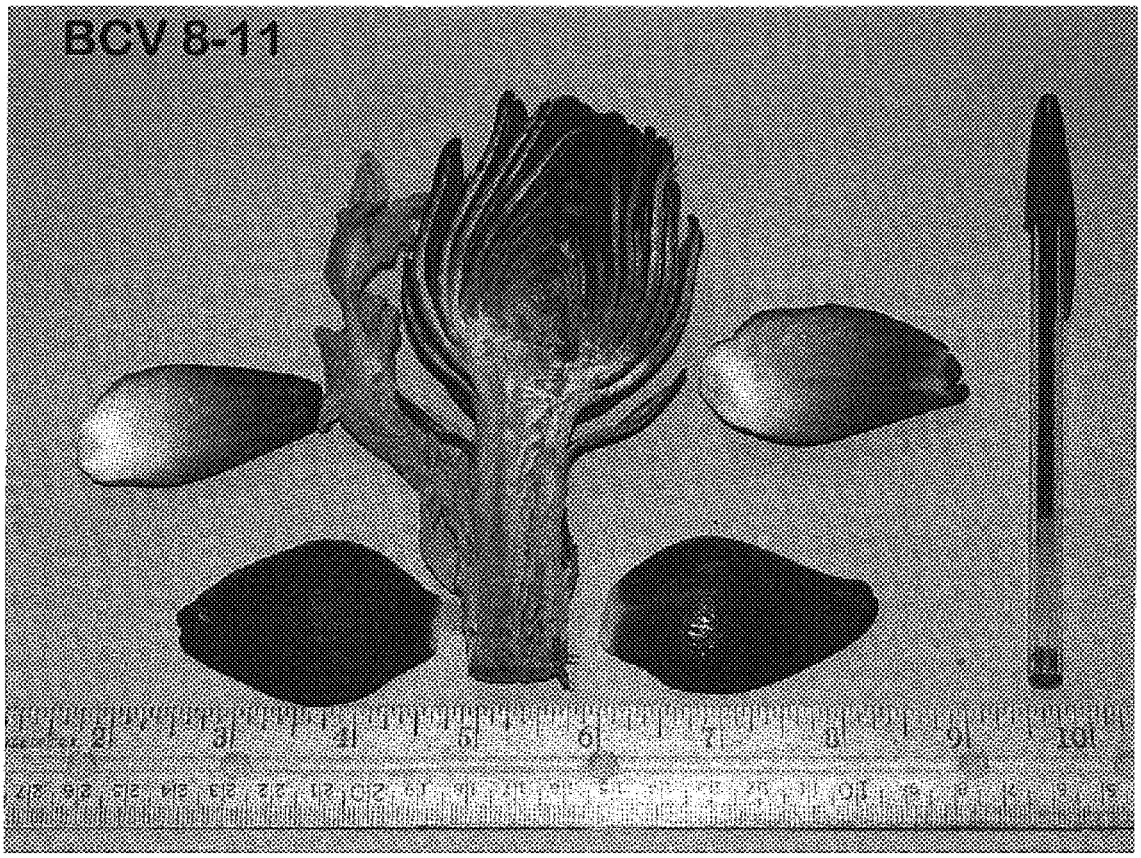
FIG. 3 shows a close-up view of the vertical cross-section of 'BCV 8-11's fruit in full color.
Figure 4:
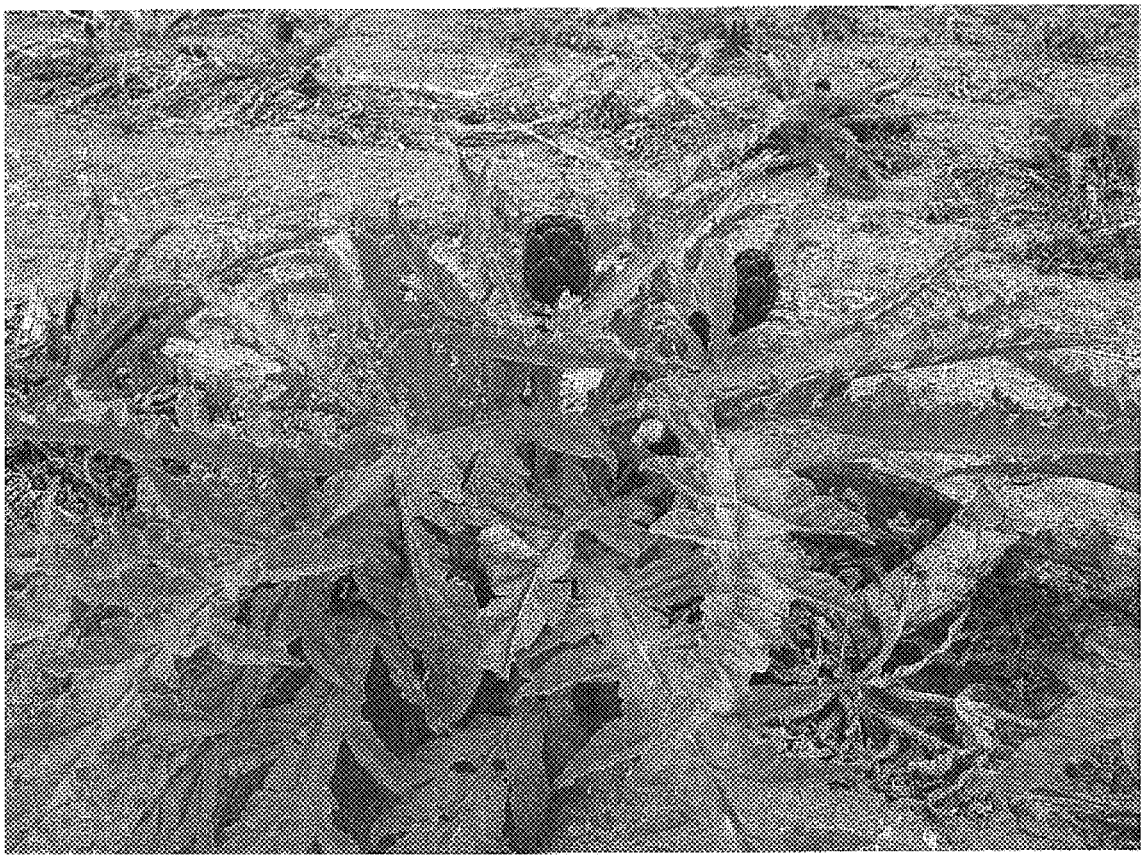
FIG. 4 shows a side elevational view of the 'BCV 8-11' plant in whole.

The following observations, measurements, and values describing the new artichoke plant are based upon observations of plants grown in Lompoc, Calif. The selection varietal was a single plant that was then reproduced. Selection was performed in an outdoor field setting. Unless otherwise indicated, the data were collected from plants that originated from asexually reproduced plants that had been grown in Perpignan by micropropagation, acclimatized in California, and then vegetatively divided. The plants were grown in the soil in rows where row spacing (bed centers) was at 80 inches, and individual plant spacing at 36 inches. Unless otherwise indicated, the measurements described herein were obtained from plants grown in accordance with the following: after acclimatization, plants were planted in the field in July 2001 and harvested in March of 2002. The plants were cut back and split. New plants were planted in July of 2002 and measurements performed in December of 2002 or January of 2003. Color references are measured against The Royal Horticultural Society Colour Chart.

Plant growth is indicated below as "moderate". Exemplary growth data showed that plants planted from tissue culture on Jun. 9, 2004 grew to an average of 47 inches in height and 86 inches in width by Jan. 26, 2005; and plants planted from tissue culture on Jul. 29, 2004 grew to an average of 41 inches in height and 87 inches in width by Jan. 26, 2005.

General:
- *Parentage*.—Seed parent: 'Violet de Provence'. Pollen parent: 'Violet de Provence'.
- *Classification*.—*Cynara Scolymus* L.
- *Propagation*.—Asexual production by tissue culture.
- *Height*.—116.8 to 147.3 cm; average 128.7 cm.
- *Width*.—182.9 to 241.3 cm; average 213.9 cm.
- *Form*.—Full.
- *Growth habit*.—Upright with some lateral spread of leaves and shoots.
- *Plant vigor*.—Moderate.

Main stem:
- *Main stem length*.—Approximately 94.0 to 121.9 cm.
- *Main stem width* (*w/leaves*).—Approximately 34.3 to 47.0 cm.
- *Main stem diameter*.—5.4 to 7.1 cm; average 6.6 cm.
- *Average internode distance*.—Approximately 6.1 to 8.9 cm; mean 6.0 cm.

Side shoots:
- *Development*.—Moderate.
- *Color*.—Yellow green group 147B.
- *Number*.—Average of 6.8 shoots per plant.
- *Length*.—12 to 34 cm; mean 26 cm.
- *Diameter*.—1.2 to 2.8 cm; mean 2.0 cm.
- *No. of leaves per shoot*.—2 to 6 leaves.
- *Average internode distance*.—3.5 to 5.4 cm.

Capitulum:
- *Size* (*primary*).—Approximately 9.0 cm.
- *Shape*.—Oval with reflexive bracts.
- *Weight*.—150 to 200 gm.
- *Texture*.—Smooth, Felt-like.
- *Fragrance*.—Mild with vegetative or grassy overtones.

Bract:
- *Length*.—Approximately 7 cm.
- *Width*.—Approximately 5 cm.
- *Shape*. —Triangular to oval, longer than broad, and thick.
- *Texture*. —Smooth with more texture like felt.
- *Number*.—102 per head.
- *Color* (*inner*).—Greyed purple group between 187B and 187C.
- *Color* (*outer*).—Greyed purple group between 187A and 187B.
- *Firmness*.—Less Firm and fleshy with thinner basal thickness.
- *Spinosity*.—None, or minimal — less than 1 mm.
- *Basal thickness*.—6 to 17 mm.

Miscellaneous:
- *Heart description*.—Concave full, well developed with thick bract connection.
- *Receptacle thickness*.—0.9 cm.
- *Heart color*.—Yellow green group between 150B and 150C.
- *Florets*.—Sterile.
- *Pappus length*.—0.8 cm.
- *Pappus color*.—Yellow green group 150D.
- *Head firmness*.—Firm, heads are dense and solid.
- *Gloss*.—Less glossy than 'Green Globe' (unpatented).
- *Cold storage response*.—Minor brown coloration on the cut stem. Overall less glossy.
- *Head response* (*weather*).—After frosts the outer epidermal layer would crinkle and blister, but not discolored.

*Disease*.—Older leaves are susceptible to *Ramularia* leaf spot.

*Bud burst*.—March 10 to March 30.

Foliage:

*Leaf shape*.—Long narrow, slightly oval with multiple lobes such that the outer edges appear coarsely serrated; the apex is pointed and the petiole attaches to the center of a slightly obcordate base.

*Density*.—Dense, many large leaves off main stem with leafy side shoots development as well.

*No. of leaves on main stem*.—9 to 18 leaves.

*Distance between main lobes*.—Approximately 6.8 to 8.9 cm.

*Leaf ratio*.—Approximately 2.7 to 3.7 cm.

*Leaf area*.—Approximately 1,714 to 2,561 cm sq.

*Upper leaf surface color*.—Green group between 139B and 139C.

*Lower leaf surface color*.—Green group between 138B and 138C.

*Texture*.—Waxy leaf margins with a rough or crinkly intervenal texture.

*Pubescence*.—Leaves more pubescent than 'Green Globe'.

*Lobe width*.—Approximately 8.6 to 11.4 cm.

*Lobe indentation*.—Approximately 4.2 to 4.4 cm.

*Petiole length*.—Approximately 20.3 to 25.4 cm.

*Petiole width*. —Approximately 2.5 to 3.8 cm.

*Petiole thickness*.—Approximately 1.0 to 2.1 cm.

*Petiole texture*.—Spindled, wherein multiple ridges that are parallel to the lengthwise orientation, radiate around the petiole.

*Petiole color*.—Interior: Yellow green group 145A; outer surface, underside: Yellow green group between 145B and 145C; outer surface, upper side: Yellow green group 145B and 145C are each individually present.

What is claimed is:

1. The new and distinct variety of artichoke plant substantially as shown and described.

* * * * *